(12) United States Patent
Young et al.

(10) Patent No.: US 7,442,776 B2
(45) Date of Patent: Oct. 28, 2008

(54) CANCEROUS DISEASE MODIFYING ANTIBODIES

(76) Inventors: David S. F. Young, 33 University Avenue, Suite 2407, Toronto, Ontario (CA) M5J 2S7; Susan E. Hahn, 9 Innisfree Court, Toronto, Ontario (CA) M6P 3N7; Helen P. Findlay, 205 Glendonwynne Road, Toronto, Ontario (CA) M6P 3E9

( * ) Notice: Subject to any disclaimer, the term of this patent is extended or adjusted under 35 U.S.C. 154(b) by 396 days.

(21) Appl. No.: 10/810,163

(22) Filed: Mar. 26, 2004

(65) Prior Publication Data

US 2004/0180002 A1 Sep. 16, 2004

Related U.S. Application Data

(63) Continuation-in-part of application No. 10/713,642, filed on Nov. 13, 2003, now Pat. No. 7,256,272, which is a continuation of application No. 09/727,361, filed on Nov. 29, 2000, now Pat. No. 6,657,048, which is a continuation-in-part of application No. 09/415,278, filed on Oct. 8, 1999, now Pat. No. 6,180,357.

(51) Int. Cl.
*C07K 16/00* (2006.01)

(52) U.S. Cl. .................................. 530/388.1; 424/130.1

(58) Field of Classification Search ........................ None
See application file for complete search history.

(56) References Cited

U.S. PATENT DOCUMENTS

| | | | |
|---|---|---|---|
| 4,172,124 A | 10/1979 | Koprowski et al. | |
| 4,861,581 A | 8/1989 | Epstein et al. | |
| 5,171,665 A | 12/1992 | Hellstrom et al. | |
| 5,484,596 A | 1/1996 | Hanna, Jr. et al. | |
| 5,693,763 A | 12/1997 | Codington et al. | |
| 5,750,102 A | 5/1998 | Eisenbach et al. | |
| 5,780,033 A | 7/1998 | Torchilin et al. | |
| 5,783,186 A | 7/1998 | Arakawa et al. | |
| 5,849,876 A | 12/1998 | Linsley et al. | |
| 5,869,045 A | 2/1999 | Hellstrom et al. | |
| 5,869,268 A | 2/1999 | Kudo et al. | |
| 6,180,357 B1 | 1/2001 | Young et al. | |
| 6,657,048 B2 | 12/2003 | Young et al. | |

FOREIGN PATENT DOCUMENTS

WO     WO95/20401     8/1995

OTHER PUBLICATIONS

Weiner (Seminars Oncology, vol. 26, No. 4, 1999, pp. 41-50).*
Osband and Ross (Immunology Today, 1990, 11:193-195).*
Gura (Science, 1997, 278:1041-1042).*
Kaiser (Science, 2006, 313, 1370).*
White et al. (2001, Ann. Rev. Med., 2001, 52:125-145).*
D. Harris et al, "Serotherapy of cancer", Seminars in Oncology, 16(3):180-198 (Jun. 1989).

H. Dvorak et al, "Structure of solid tumors and their vasculature: implications for therapy with monoclonal antibodies", Cancer Cells, 3(3):77-85 (Mar. 1991).
S. Engelholm et al, "Disaggregation of human solid tumours by combined mechanical and enzymatic methods", Br. J. Cancer, 51:93-98 (1985).
A. Costa et al, "Implications of disaggregation procedures on biological representation of human solid tumours", Cell Tisue Kinet., 20:171-180 (1987).
S. Dairkee et al, "Partial enzymatic degradation of stroma allows enrichment and expansion of primary breast tumor cells", Cancer Research, 57:1590-1596 (Apr. 1997).
B. Franzen et al, "Nonenzymatic extraction of cells from clinical tumor material for analysis of gene expression by two-dimensional polyacrylamide gel electrophoresis", Electrophoresis, 14:1045-1053 (1993).
E. Holz et al, "Antibody-based immunotherapeutic strategies in colorectal cancer", Recent Results in Cancer Research, 142:381-400 (1996).
R. Dillman, "Antibodies as cytotoxic therapy", J. Clin. Oncol., 12(7):1497-1515 (Jul. 1994).
R. Dillman, "Monoclonal antibodies for treating cancer", Annals of Internal Medicine, 111:592-603 (1999).
M. Disis et al, "HER-2/neu protein: a target for antigen-specific immunotherapy of human cancer", Advances in Cancer Research, 71:343-371 (1997).
A. Begg et al, "Rapid fluorescence-based assay for radiosensitivity and chemosensitivity testing in mammalian cells in vitro", Cancer Research, 49:565-569 (Feb. 1989).
J. Cruse et al, Illustrated Dictionary of Immunology, CRC Press, p. 280 (1995).
A. Knuth et al, "ADCC reactivity of human melanoma cels with mouse monoclonal antibodies", Proc. Am. Assoc. Cancer Res., 25:1005 (Mar. 1984) Abstract only.
J. Horoszewicz et al, "Monoclonal antibodies to a new antigenic marker in epithelial prostatic cells and serum of prostatic cancer patients", Anticancer Research, 7:927-936 (1987).
D. Herlyn et al, "Monoclonal anticolon carcinoma antibodies in complement-dependent cytotoxicity", Int. J. Cancer, 27:769-774 (1981).

(Continued)

*Primary Examiner*—Larry R. Helms
*Assistant Examiner*—Meera Natarajan
(74) *Attorney, Agent, or Firm*—McHale & Slavin, P.A.

(57) ABSTRACT

The present invention relates to a method for producing patient cancerous disease modifying antibodies using a novel paradigm of screening. By segregating the anti-cancer antibodies using cancer cell cytotoxicity as an end point, the process makes possible the production of anti-cancer antibodies for therapeutic and diagnostic purposes. The antibodies can be used in aid of staging and diagnosis of a cancer, and can be used to treat primary tumors and tumor metastases. The anti-cancer antibodies can be conjugated to toxins, enzymes, radioactive compounds, and hematogenous cells.

8 Claims, 4 Drawing Sheets

OTHER PUBLICATIONS

V. Kravtsov et al, "Automated monitoring of apoptosis in suspension cell cultures", Laboratory Investigation, 74(2):557-570 (1996).

L. Hartwell et al, "Integrating genetic approaches into the discovery of anticancer drugs", Science, 278:1064-1068 (Nov. 1997).

B. Curti, "Physical barriers to drug delivery in tumors", Critical Reviews in Oncology/Hematology, 14:29-39 (1993).

R. Jain, "Barriers to drug delivery in solid tumors", Scientific American, 271(1):58-65 (Jul. 1994).

T. Gura, "Systems for identifying new drugs are often faulty", Science, 278:1041-1042 (Nov. 1997).

G. Dermer, "Another anniversary for the war on cancer", Bio/Technology, 12:320 (Mar. 1994).

R. Freshney, "Culture of animal cells", a Manual of Basic Technique, Alan R. Liss, Inc., New York, p. 3 (1983).

T. Hsu, "Karyology of cells in culture—a preparation and analysis of karyotypes and idiograms", in Tissue Culture Methods and Applications, eds. Kruse and Patterson, Academic Press, New York, pp. 764-767 (1973).

M. Embleton, "Monoclonal antibodies to osteogenic sarcoma antigens", Immunol. Ser., 23:181-207 (1984).

H. Drexler, "Recent results on the biology of Hodgkin and Reed-Sternberg cells", Leukemia and Lymphoma, 9:1-25 (1993).

C. Badger et al, "Prospects for monoclonal antibody therapy of leukemia and lymphoma", Cancer, 58:584-589 (1986).

E. Boven et al, "Monoclonal antibodies in cancer treatment: where do we stand after 10 years?", Radiotherapy and Oncology, 5:109-117 (1986).

A. Epstein et al, "Two new monoclonal antibodies, Lym-1 and Lym-2, reactive with human B-lymphocytes and derived tumors, with immunodiagnostic and immunotherapeutic potential", Cancer Research, 47:830-840 (1987).

K. Foon, "Biological therapy of cancer", Breast Cancer Research & Treatment, 7:5-14 (1986).

\* cited by examiner

CANCEROUS DISEASE MODIFYING ANTIBODIES

REFERENCE TO RELATED APPLICATIONS

This application is a continuation-in-part of application Ser. No. 10/713,642, filed Nov. 13, 2003, now U.S. Pat. No. 7,256,272, issued Aug. 14, 2007, which is a continuation of application Ser. No. 09/727,361, filed Nov. 29, 2000, now U.S. Pat. No. 6,657,048, which is a continuation-in-part of application Ser. No. 09/415,278, filed Oct. 8, 1999, now U.S. Pat. No. 6,180,357 B1, the contents of each of which are herein incorporated by reference.

FIELD OF THE INVENTION

This invention relates to the isolation and production of cancerous disease modifying antibodies (CDMAB) and to the use of these CDMAB in therapeutic and diagnostic processes, optionally in combination with one or more chemotherapeutic agents. The invention further relates to binding assays which utilize the CDMAB of the instant invention.

BACKGROUND OF THE INVENTION

Each individual who presents with cancer is unique and has a cancer that is as different from other cancers as that person's identity. Despite this, current therapy treats all patients with the same type of cancer, at the same stage, in the same way. At least 30 percent of these patients will fail the first line therapy, thus leading to further rounds of treatment and the increased probability of treatment failure, metastases, and ultimately, death. A superior approach to treatment would be the customization of therapy for the particular individual. The only current therapy that lends itself to customization is surgery. Chemotherapy and radiation treatment cannot be tailored to the patient, and in most cases, surgery by itself is inadequate for producing cures.

With the advent of monoclonal antibodies, the possibility of developing methods for customized therapy became more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens. This has given rise to the belief that monoclonal antibodies can serve as "Magic Bullets" to eliminate cancer cells.

Monoclonal antibodies isolated in accordance with the teachings of the instantly disclosed invention have been shown to modify the cancerous disease process in a manner which is beneficial to the patient, for example by reducing the tumor burden, and will variously be referred to herein as cancerous disease modifying antibodies (CDMAB) or "anticancer" antibodies.

At the present time, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. Such a course of therapy would, ideally, increase the rate of cures, and produce better outcomes, thereby satisfying a long-felt need.

Historically, the use of polyclonal antibodies has been used with limited success in the treatment of human cancers. Lymphomas and leukemias have been treated with human plasma, but there were few prolonged remission or responses. Furthermore, there was a lack of reproducibility and no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least 4 clinical trials for human breast cancer which produced only 1 responder from at least 47 patients using antibodies against specific antigens or based on tissue selectivity. It was not until 1998 that there was a successful clinical trial using a humanized anti-her 2 antibody in combination with cisplatin. In this trial 37 patients were accessed for responses of which about a quarter had a partial response rate and another half had minor or stable disease progression.

The clinical trials investigating colorectal cancer involve antibodies against both glycoprotein and glycolipid targets. Antibodies such as 17-1A, which has some specificity for adenocarcinomas, has undergone Phase 2 clinical trials in over 60 patients with only 1 patient having a partial response. In other trials, use of 17-1A produced only 1 complete response and 2 minor responses among 52 patients in protocols using additional cyclophosphamide. Other trials involving 17-1A yielded results that were similar. The use of a humanized murine monoclonal antibody initially approved for imaging also did not produce tumor regression. To date there has not been an antibody that has been effective for colorectal cancer. Likewise there have been equally poor results for lung, brain, ovarian, pancreatic, prostate, and stomach cancers. There has been some limited success in the use of anti-GD3 monoclonal antibodies for melanoma. Thus, it can be seen that despite successful small animal studies that are a prerequisite for human clinical trials, the antibodies that have been tested thus far, have been for the most part, ineffective.

Prior Patents:

U.S. Pat. No. 5,750,102 discloses a process wherein cells from a patient's tumor are transfected with MHC genes which may be cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung, while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas is not dependent upon the epithelial tissue of origin.

U.S. Pat. No. 5,783,186 is drawn to anti-Her2 antibodies which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for generating a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single chain immunotoxins reactive with human carcinoma cells. The mechanism by which these antibodies function is two-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an anti-nuclear autoantibody from an aged mammal. In this case, the autoantibody is said to be one type of natural antibody found in the immune system. Because the autoantibody comes from "an aged mammal", there is no requirement that the autoantibody actually comes from the patient being treated. In addition the patent discloses natural and monoclonal anti-nuclear autoantibody from an aged mammal, and a hybridoma cell line producing a monoclonal anti-nuclear autoantibody.

SUMMARY OF THE INVENTION

The instant inventors have previously been awarded U.S. Pat. No. 6,180,357, entitled "Individualized Patient Specific Anti-Cancer Antibodies" directed to a process for selecting individually customized anti-cancer antibodies which are useful in treating a cancerous disease. For the purpose of this document, the terms "antibody" and "monoclonal antibody" (mAb) may be used interchangeably and refer to intact immunoglobulins produced by hybridomas (e.g. murine or human), immunoconjugates and, as appropriate, immunoglobulin fragments and recombinant proteins derived from immunoglobulins, such as chimeric and humanized immunoglobulins, F(ab') and F(ab')$_2$ fragments, single-chain antibodies, recombinant immunoglobulin variable regions (Fv)s, fusion proteins etc. For the purpose of this document, the term "tissue sample" is understood to mean at least one cell or an aggregate of cells obtained from a mammal. It is well recognized in the art that some amino acid sequence can be varied in a polypeptide without significant effect on the structure or function of the protein. In the molecular rearrangement of antibodies, modifications in the nucleic or amino acid sequence of the backbone region can generally be tolerated. These include, but are not limited to, substitutions (preferred are conservative substitutions), deletions or additions. Furthermore, it is within the purview of this invention to conjugate standard chemotherapeutic modalities, e.g. radionuclides, with the CDMAB of the instant invention, thereby focusing the use of said chemotherapeutics. The CDMAB can also be conjugated to toxins, cytotoxic moieties, enzymes e.g. biotin conjugated enzymes, or hematogenous cells, thereby forming antibody conjugates. Such conjugated moieties are illustrated herein as conjugated to the monoclonal antibody derived from the hybridoma cell line designated 6BD-25; similar antibody conjugates could be formed utilizing the monoclonal antibody derived from the hybridoma cell line designated 5LAC-23.

This application utilizes the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies and/or a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

Using substantially the process of U.S. Pat. No. 6,180,370 and as outlined in U.S. Pat. No. 6,657,048, the mouse monoclonal antibodies 6BD-25 and 5LAC-23 were obtained following immunization of mice with cells from a patient's breast and lung tumor biopsy respectively. The 6BD-25 antigen was initially not detected on a variety of human normal and cancer cell lines by cell ELISA/FACS. After increasing the sensitivity of the assay through conjugation of the 6BD-25 antibodies to biotin, the antigen was detected on the breast cancer cell line MDA-MB-231 and the ovarian cancer cell lines C-13, OVCA-429 and OV2008. The breast cancer cell line Hs574.T was susceptible to the cytotoxic effects of unpurified 6BD-25. The breast cancer cell line MCF-7, the ovarian cancer cell line OVCAR-3 and the colon cancer cell line SW1116 were the only 3 cancer cell lines tested that were susceptible to the cytotoxic effects of purified 6BD-25. Through the use of FACS analysis, the antigen for 5LAC-23 was detected on the SW620 colon cancer cell line and not on any of the other cell lines tested. The breast (Hs574.T), lung (NCI-H661) and skin (A2058) cancer cell line were susceptible to the cytotoxic effects of unpurified 5LAC-23. The ovarian cancer cell line OVCAR-3 was the only cancer cell line tested that was susceptible to the cytotoxic effects of purified 5LAC-23.

The result of 6BD-25 cytotoxicity against OVCAR-3 and SW1116 cells in culture was further extended by its anti-tumor activity towards these cells when transplanted into mice. In an in vivo model of colon cancer, the human SW1116 cells were implanted subcutaneously at the scruff of the neck while for an in vivo model of ovarian cancer, the human OVCAR-3 cells were implanted intraperitoneally. For both models, immunodeficient mice were used as they are incapable of rejecting the human tumor cells due to a lack of certain immune cells. Pre-clinical xenograft tumor models are considered valid predictors of therapeutic efficacy. Xenografts in mice grow as solid tumors developing stroma, central necrosis and neo-vasculature. The tumor cell lines OVCAR-3 and SW1116 have been evaluated as an in vivo xenograft model in immunodeficient mice. The good engraftment or 'take-rate' of the OVCAR-3 and SW1116 tumors and the sensitivity of the tumors to standard chemotherapeutic agents have characterized them as suitable models. The parental cell line and variants of the cell line have been used in xenograft tumor models to evaluate a wide range of therapeutic agents.

In the preventative in vivo model of human colon cancer, 6BD-25 was given to mice one day prior to implantation of tumor cells followed by weekly injections for a period of 7 weeks. 6BD-25 treatment was significantly (p=0.001) more effective in suppressing tumor growth during the treatment period than buffer control. At the end of the treatment phase, mice given 6BD-25 had tumors that grew to only 54 percent of the control group. During the post treatment follow-up period, the treatment effects of 6BD-25 were sustained and the mean tumor volume in the treated groups continued to be significantly smaller than controls until the end of the measurement phase (p=0.002). 6BD-25 treatment appeared safe, as it did not induce any signs of toxicity, including reduced body weight or other signs of clinical distress. Thus, 6BD-25 treatment was efficacious as it delayed tumor growth compared to the control-treated group in a well-established model of human colon cancer.

Besides the preventative in vivo tumor model of colon cancer, 6BD-25 demonstrated anti-tumor activity against OVCAR-3 cells in a preventative ovarian in vivo tumor model. In this xenograft tumor model, OVCAR-3 ovarian cancer cells were transplanted intraperitoenally into immunodeficient mice with treatment commencing the day after implantation for a total of 10 doses. Treatment with 6BD-25 was compared to a buffer control. Body weight was used as a surrogate measure of tumor progression. Increased body weight is indicative of tumor burden since the weight gain is caused by ascites formation. At day 80 post-implantation (16 days after the end of treatment), the mice in the treatment group had body weights significantly less than the control group (p=0.002). There was also a significant survival benefit with treatment of 6BD-25 versus the buffer control (p<0.02). Again, 6BD-25 treatment appeared safe, as it did not induce any signs of toxicity or clinical distress. The anti-tumor activity of 6BD-25 and its apparent lack of toxicity make it an attractive anti-cancer therapeutic agent.

In all, this invention teaches the use of the 6BD-25 and 5LAC-23 antigens as targets for therapeutic agents and that when administered, 6BD-25 can reduce the tumor burden in a mammal with a cancer expressing the antigen, and can also lead to prolonged survival of the treated mammal. The efficacy of 6BD-25 treatment in vivo and the concomitant undetectable or low level of antigen expression on the SW1116 and OVCAR-3 cells respectively, illustrates that the level of antigen expression does not necessarily correlate with in vivo efficacy. Furthermore, this invention also teaches that detecting the 6BD-25 and 5LAC-23 antigen in cancerous cells can be useful for the diagnosis, prediction of therapy, and prognosis of mammals bearing tumors that express this antigen.

If a patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and anti-cancer antibodies conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody-dependent cell-mediated cytotoxicity (ADCC) or complement-dependent cytotoxicity (CDC). For example murine IgM and IgG2a antibodies can activate human complement by binding the C-1 component of the complement system thereby activating the classical pathway of complement activation which can lead to tumor lysis. For human antibodies, the most effective complement-activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody-mediated cancer killing may be through the use of antibodies that function to catalyze the hydrolysis of various chemical bonds in the cell membrane and its associated glycoproteins or glycolipids, so-called catalytic antibodies.

There are two additional mechanisms of antibody-mediated cancer cell killing which are more widely accepted. The first is the use of antibodies as a vaccine to induce the body to produce an immune response against the putative antigen that resides on the cancer cell. The second is the use of antibodies to target growth receptors and interfere with their function or to down regulate that receptor so that its function is effectively lost.

The clinical utility of a cancer drug is based on the benefit of the drug under an acceptable risk profile to the patient. In cancer therapy survival has generally been the most sought after benefit, however there are a number of other well-recognized benefits in addition to prolonging life. These other benefits, where treatment does not adversely affect survival, include symptom palliation, protection against adverse events, prolongation in time to recurrence or disease-free survival, and prolongation in time to progression. These criteria are generally accepted and regulatory bodies such as the U.S. Food and Drug Administration (F.D.A.) approve drugs that produce these benefits (Hirschfeld et al. Critical Reviews in Oncology/Hematolgy 42:137-143 2002). In addition to these criteria it is well recognized that there are other endpoints that may presage these types of benefits. In part, the accelerated approval process granted by the U.S. F.D.A. acknowledges that there are surrogates that will likely predict patient benefit. As of year-end (2003), there have been sixteen drugs approved under this process, and of these, four have gone on to full approval, i.e., follow-up studies have demonstrated direct patient benefit as predicted by surrogate endpoints. One important endpoint for determining drug effects in solid tumors is the assessment of tumor burden by measuring response to treatment (Therasse et al. Journal of the National Cancer Institute 92(3):205-216 2000). The clinical criteria (RECIST criteria) for such evaluation have been promulgated by Response Evaluation Criteria in Solid Tumors Working Group, a group of international experts in cancer. Drugs with a demonstrated effect on tumor burden, as shown by objective responses according to RECIST criteria, in comparison to the appropriate control group tend to, ultimately, produce direct patient benefit. In the pre-clinical setting tumor burden is generally more straightforward to assess and document. In that pre-clinical studies can be translated to the clinical setting, drugs that produce prolonged survival in pre-clinical models have the greatest anticipated clinical utility. Analogous to producing positive responses to clinical treatment, drugs that reduce tumor burden in the pre-clinical setting may also have significant direct impact on the disease. Although prolongation of survival is the most sought after clinical outcome from cancer drug treatment, there are other benefits that have clinical utility and it is clear that tumor burden reduction, which may correlate to a delay in disease progression, extended survival or both, can also lead to direct benefits and have clinical impact (Eckhardt et al. Developmental Therapeutics: Successes and Failures of Clinical Trial Designs of Targeted Compounds; ASCO Educational Book, 39th Annual Meeting, 2003, pages 209-219).

Accordingly, it is an objective of the invention to utilize a method for producing cancerous disease modifying antibodies from cells derived from a particular individual which are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach CDMAB and antigen binding fragments thereof.

It is a further objective of the instant invention to produce CDMAB whose cytotoxicity is mediated through ADCC.

It is yet an additional objective of the instant invention to produce CDMAB whose cytotoxicity is mediated through CDC.

It is still a further objective of the instant invention to produce CDMAB whose cytotoxicity is a function of their ability to catalyze hydrolysis of cellular chemical bonds.

A still further objective of the instant invention is to produce CDMAB which are useful in a binding assay for diagnosis, prognosis, and monitoring of cancer.

Other objects and advantages of this invention will become apparent from the following description wherein, by way of illustration and example, certain embodiments of this invention are set forth.

DETAILED DESCRIPTION OF THE INVENTION

EXAMPLE 1

Hybridoma Production—Hybridoma Cell Lines: 6BD-25 and 5LAC-23

The hybridoma cell lines 6BD-25 and 5LAC-23 were deposited, in accordance with the Budapest Treaty, with the American Type Culture Collection (ATCC), 10801 University Blvd., Manassas, Va. 20110-2209 on Dec. 9, 2003, under Accession Number PTA-5691 and PTA-5690 respectively. In accordance with 37 CFR 1.808, the depositors assure that all restrictions imposed on the availability to the public of the deposited materials will be irrevocably removed upon the granting of a patent. The derivation of the clone, the supernatant and cell ELISA screening of 6BD-25 and 5LAC-23 has previously been described in U.S. Pat. No. 6,657,048.

6BD-25 and 5LAC-23 monoclonal antibodies were produced by culturing the hybridomas in CL-1000 flasks (BD Biosciences, Oakville, ON) with collections and reseeding occurring twice/week. The antibodies were purified according to standard antibody purification procedures with Protein G Sepharose 4 Fast Flow (Amersham Biosciences, Baie d'Urfé, QC).

6BD-25 and 5LAC-23 were compared to a number of both positive (anti-Fas (EOS9.1, IgM, kappa, 20 micrograms/mL, eBioscience, San Diego, Calif.), anti-EGFR (C225, IgG1, kappa, 5 microgram/mL, Cedarlane, Hornby, ON), Cycloheximide (100 micromolar, Sigma, Oakville, ON), $NaN_3$ (0.1%, Sigma, Oakville, ON)) and negative (107.3 (anti-TNP, IgG1, kappa, 20 microgram/mL, BD Biosciences, Oakville, ON), G155-178 (anti-TNP, IgG2a, kappa, 20 microgram/mL, BD Biosciences, Oakville, ON), MPC-11 (antigenic specificity unknown, IgG2b, kappa, 20 microgram/mL), J606 (anti-fructosan, IgG3, kappa, 20 microgram/mL), IgG Buffer (2%), IgM buffer (2%)) controls in a cytotoxicity assay (Table 1). Breast cancer (MDA-MB-231 (MB-231), MDA-MB-468 (MB-468), MCF-7), colon cancer (HT-29, SW1116, SW620), lung cancer (NCI-H460), ovarian cancer (OVCAR-3), prostate cancer (PC-3), and non-cancer (CCD-27sk, Hs888.Lu) cell lines were tested (all from the ATCC, Manassas, Va.). The Live/Dead cytotoxicity assay was obtained from Molecular Probes (Eugene, Oreg.). The assays were performed according to the manufacturer's instructions with the changes outlined below. Cells were plated before the assay at the predetermined appropriate density. After 2 days, purified antibody or controls were diluted into media, and then 100 microliters were transferred to the cell plates and incubated in a 5 percent $CO_2$ incubator for 5 days. The plate was then emptied by inverting and blotted dry. Room temperature DPBS containing MgCl$_2$ and CaCl$_2$ was dispensed into each well from a multi-channel squeeze bottle, tapped three times, emptied by inversion and then blotted dry. 50 microliters of the fluorescent calcein dye diluted in DPBS containing MgCl$_2$ and CaCl$_2$ was added to each well and incubated at 37° C. in a 5 percent CO$_2$ incubator for 30 minutes. The plates were read in a Perkin-Elmer HTS7000 fluorescence plate reader and the data was analyzed in Microsoft Excel and the results were tabulated in Table 1. The data represented an average of four experiments tested in triplicate and presented qualitatively in the following fashion: 4/4 experiments greater than threshold cytotoxicity (+++), 3/4 experiments greater than threshold cytotoxicity (++), 2/4 experiments greater than threshold cytotoxicity (+). Unmarked cells in Table 1 represent inconsistent or effects less than the threshold cytotoxicity. The chemical cytotoxic agents induced their expected cytotoxicity while a number of other antibodies which were included for comparison also performed as expected given the limitations of biological cell assays. The 6BD-25 antibody demonstrated cytotoxicity in breast, ovarian and colon cancer cell lines selectively, while having no effect on non-transformed normal cells. The 5LAC-23 antibody demonstrated cytotoxicity in the ovarian cancer cell line selectively while also having no effect on non-transformed normal cells. The antibodies 6BD-25 and 5LAC-23 were selective in their activity since not all cancer cell types were susceptible. Furthermore, 6BD-25 and 5LAC-23 demonstrated functional specificity since they did not produce cytotoxicity against non-cancer cell types, which is an important therapeutic factor.

grams/mL on ice for 30 minutes. Conjugating 6BD-25 to biotin was performed with biotinylation reagent (Pierce E2-Link Sulfo-NHS-LC-biotin, Rockford, Ill.). The biotinylation reagent was added in 20 times molar excess to 6BD-25 and incubated for 2 hrs at room temperature with shaking. The biotinylated 6BD-25 was then dialyzed overnight against PBS at 4° C. Prior to the addition of Alexa Fluor 488-conjugated secondary antibody (for unconjugated primary antibodies) or streptavidin R-phycoerythrin conjugated secondary antibody (for biotinylated 6BD-25), the cells were washed once with wash media. The appropriate secondary antibody in staining media was then added for 20 minutes. The cells were then washed for the final time and resuspended in staining media containing 1 microgram/mL propidium iodide. Flow cytometric acquisition of the cells was assessed by running samples on a FACScan using the CellQuest software (BD Biosciences, Oakville, ON). The forward (FSC) and side scatter (SSC) of the cells were set by adjusting the voltage and amplitude gains on the FSC and SSC detectors. The detectors for the three fluorescence channels (FL1, FL2, and FL3) were adjusted by running cells stained with purified isotype control antibody followed by the appropriate secondary antibody such that cells had a uniform peak with a median fluorescent intensity of approximately 1-5 units. Live cells were acquired by gating for FSC and propidium iodide exclusion. For each sample, approximately 10,000 live cells were acquired for analysis and the results presented in Table 2. Table 2 tabulated the mean fluorescence intensity fold increase above isotype control and is presented qualitatively as: less than 1.5 (−); 1.5 to 2 (+); 2 to 3 (++); 3 to 10 (+++) and >10 (++++).

TABLE 1

In Vitro Cytotoxicity of 6BD-25 and 5LAC-23

| | Antibody | MB-231 | MB-468 | MCF-7 | HT-29 | SW1116 | SW620 | NCI H460 | OVCAR | PC-3 | CCD 27sk | Hs888 Lu |
|---|---|---|---|---|---|---|---|---|---|---|---|---|
| | 6BD-25 | | | + | | ++ | | | + | | | |
| | 5LAC-23 | | | | | | ++ | | | | | |
| Negative Controls | IgM buffer | + | | | | | | | | | | |
| | IgGI isotype | | | | | | | | | | | |
| Positive Controls | CHX | ++ | +++ | +++ | +++ | +++ | ++ | ++ | +++ | +++ | +++ | +++ |
| | NaN$_3$ | +++ | +++ | +++ | +++ | ++ | | +++ | +++ | +++ | | |
| | anti-EGFR | | +++ | | | +++ | | | | | ++ | |
| | anti-Fas | | | | ++ | | | | +++ | + | | |

Figure 1:
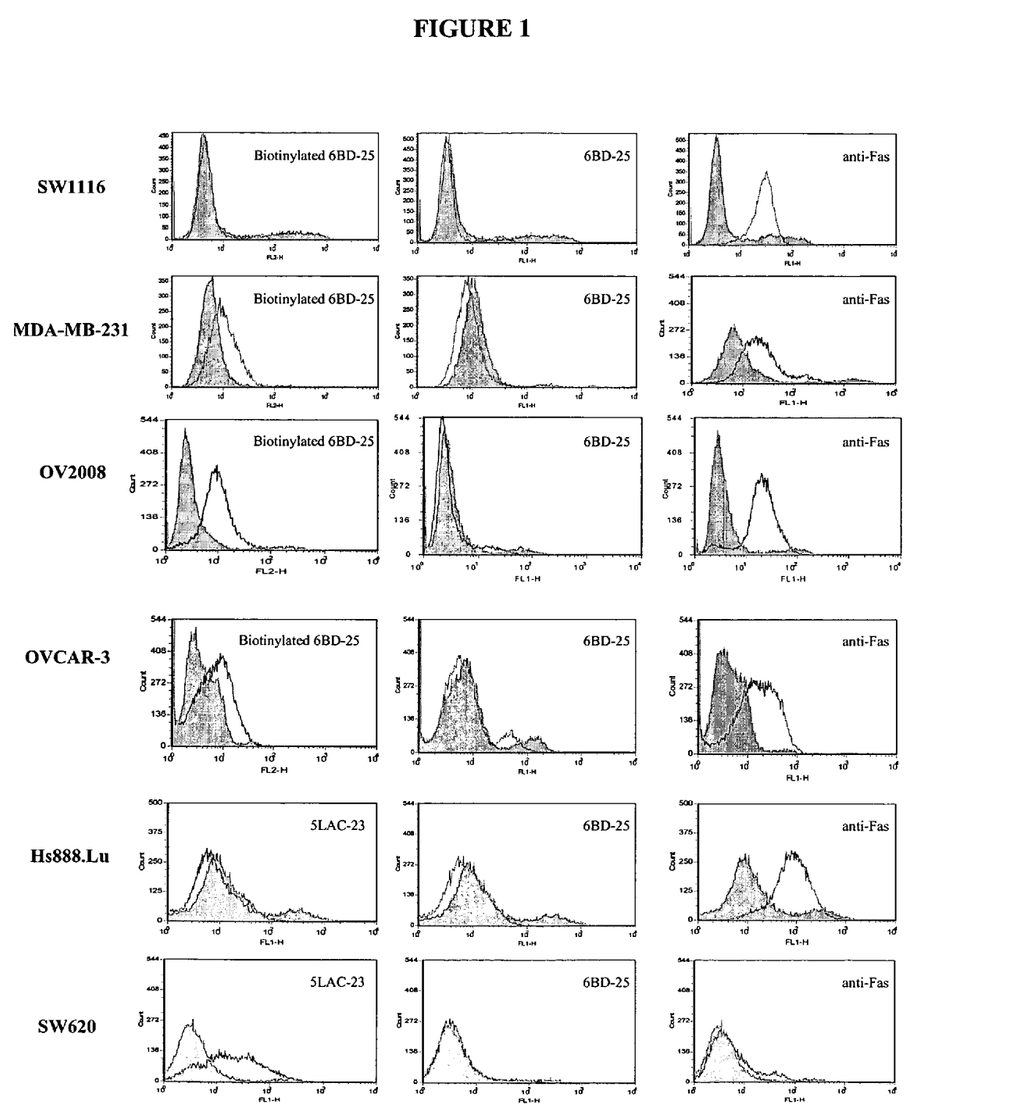
FIG. 1. Representative FACS histograms of 6BD-25, 5LAC-23 and anti-Fas (positive control) antibodies directed against several cancer and non-cancer cell lines.

Binding of 6BD-25 to the above-mentioned panel of cancer and normal cell lines was assessed by flow cytometry (FACS). Cells were prepared for FACS by initially washing the cell monolayer with DPBS (without Ca$^{++}$ and Mg$^{++}$). Cell dissociation buffer (INVITROGEN, Burlington, ON) was then used to dislodge the cells from their cell culture plates at 37° C. After centrifugation and collection, the cells were resuspended in Dulbecco's phosphate buffered saline containing MgCl$_2$, CaCl$_2$ and 25 percent fetal bovine serum at 4° C. (wash media) and counted, aliquoted to appropriate cell density, spun down to pellet the cells and resuspended in staining media (DPBS containing MgCl$_2$ and CaCl$_2$) containing 6BD-25 (unconjugated or conjugated with biotin), 5LAC-23 or control antibodies (isotype control or anti-Fas) at 20 micro- Representative histograms of 6BD-25 and 5LAC-23 antibodies were compiled for FIG. 1. Unconjugated 6BD-25 did not initially bind any cell lines tested by FACS. However, after increasing the sensitivity of the assay by conjugating 6BD-25 to biotin, it was demonstrated that a low level of antigen is present on the surface of MDA-MB-231, C-13, OVCA-429 and OV2008 cancer cells. By FACS, 5LAC-23 showed high and specific binding to the colon cancer cell line SW620. For both 6BD-25 and 5LAC-23, this was further evidence that the degree of binding was not necessarily predictive of the outcome of antibody ligation of its cognate antigen, and was a non-obvious finding. This suggested that the context of antibody ligation in different cells was determinative of cytotoxicity rather than just antibody binding.

TABLE 2

FACS Analysis of 6BD-25 and 5LAC-23

| Antibody | Isotype | CCD-27sk | PC-3 | NCI-H460 | Hs888.Lu | HT-29 | SW620 | SW1116 | MB-231 | MB-468 | MCF-7 | OV2008 | C13 | OVCA-429 | OVCAR-3 |
|---|---|---|---|---|---|---|---|---|---|---|---|---|---|---|---|
| 6BD-25 | IgM, k | − | − | − | − | − | − | − | − | − | − | − | − | − | − |
| Biotinylated 6BD-25 | IgM, k | | | | | | | − | + | − | − | +++ | + | + | + |
| 5LAC-23 | IgM, k | − | − | − | − | − | +++ | − | − | − | − | | | | − |
| anti-Fas (+ control) | IgM, k | ++++ | + | +++ | ++++ | +++ | − | +++ | ++ | + | +++ | +++ | +++ | ++ | +++ |

EXAMPLE 2

In Vivo Colon Preventative Tumor Experiments

With reference to the data shown in FIG. 2, 4 to 8 week old, female SCID mice were implanted with 5 million SW1116 human colon cancer cells in 100 microliters saline injected subcutaneously in the scruff of the neck. The mice were randomly divided into 2 treatment groups of 10. On the day prior to implantation 20 mg/kg of 6BD-25 test antibody or buffer control was administered intrapertioneally at a volume of 300 microliters after dilution from the stock concentration with a diluent that contained 500 mM NaCl, 20 mM $Na_2HPO_4.7H_2O$ and 20 mM $NaH_2PO_4.H_2O$. The antibodies were then administered once per week for a period of 7 weeks in the same fashion.

Figure 2:
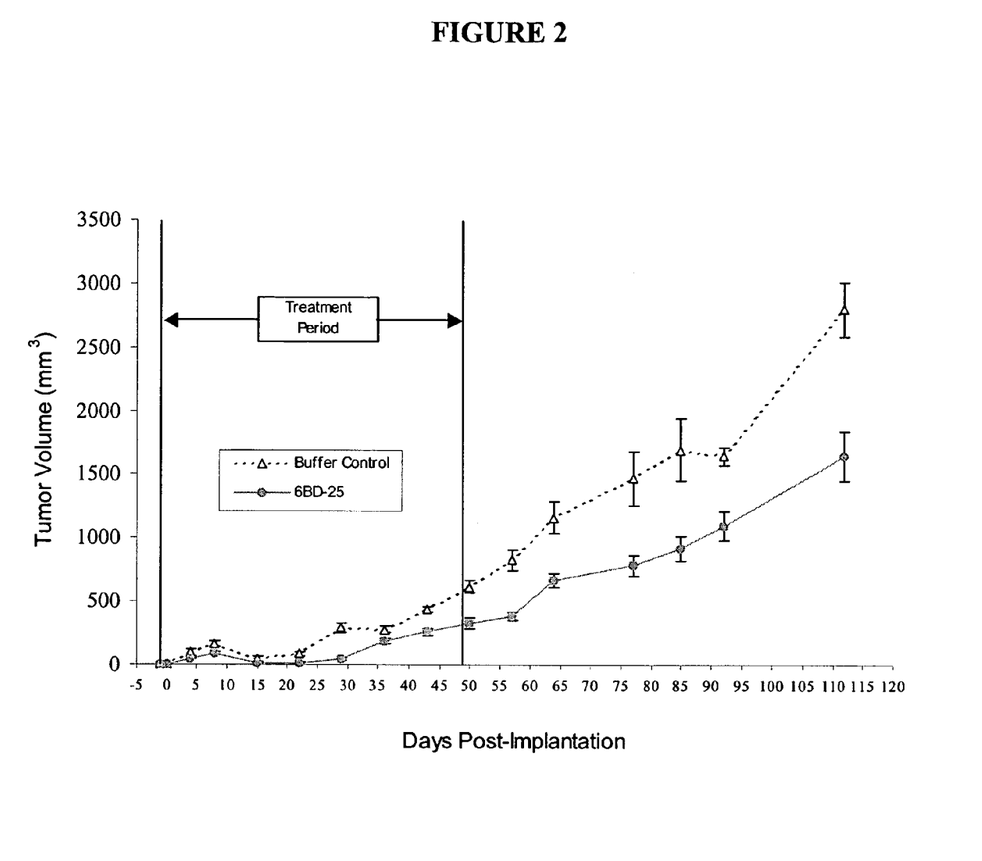
FIG. 2. Effect of 6BD-25 on tumor growth in a preventative SW1116 colon cancer model. The dashed line indicates the period during which the antibody was administered. Data points represent the mean +/−SEM.

Tumor growth was measured roughly every 7th day with calipers for up to 16 weeks or until individual animals reached the Canadian Council for Animal Care (CCAC) end-points or day 112. Body weights of the animals were recorded for the duration of the study. At the end of the study all animals were euthanised according to CCAC guidelines.

There were no clinical signs of toxicity throughout the study. Data was analyzed using the independent samples test and significance was determined using the t-test for equality of means. At day 50 (1 day after final treatment), the tumor volume in the 6BD-25 treated group was 54 percent of the buffer control (p=0.001). Delayed growth of the tumor continued past the treatment period. At day 112 (63 days post-treatment), tumor volume in the antibody treatment group was 59 percent of the buffer control (p=0.002). In summary, 6BD-25 antibody treatment reduced tumor burden in comparison to buffer control in a well-recognized model of human colon cancer. These results suggest a potential pharmacologic and pharmaceutical benefit of this antibody (6BD-25) as a therapy in other mammals, including man.

EXAMPLE 3

In Vivo Ovarian Preventative Tumor Experiments

With reference to the data shown in FIGS. 3 and 4, 4 to 8 week old, female SCID mice were implanted with 5 million OVCAR-3 human ovarian cancer cells in 1000 microliters saline injected intraperitoneally. The mice were randomly divided into 2 treatment groups of 10. On the day after implantation 20 mg/kg of 6BD-25 test antibody or antibody buffer was administered intraperitoneally at a volume of 300 microliters after dilution from the stock concentration with a diluent that contained 500 mM NaCl, 20 mM $Na_2HPO_4.7H_2O$ and 20 mM $NaH_2PO_4.H_2O$. The antibodies were then administered once per week for a period of 9 weeks in the same fashion.

Figure 3:
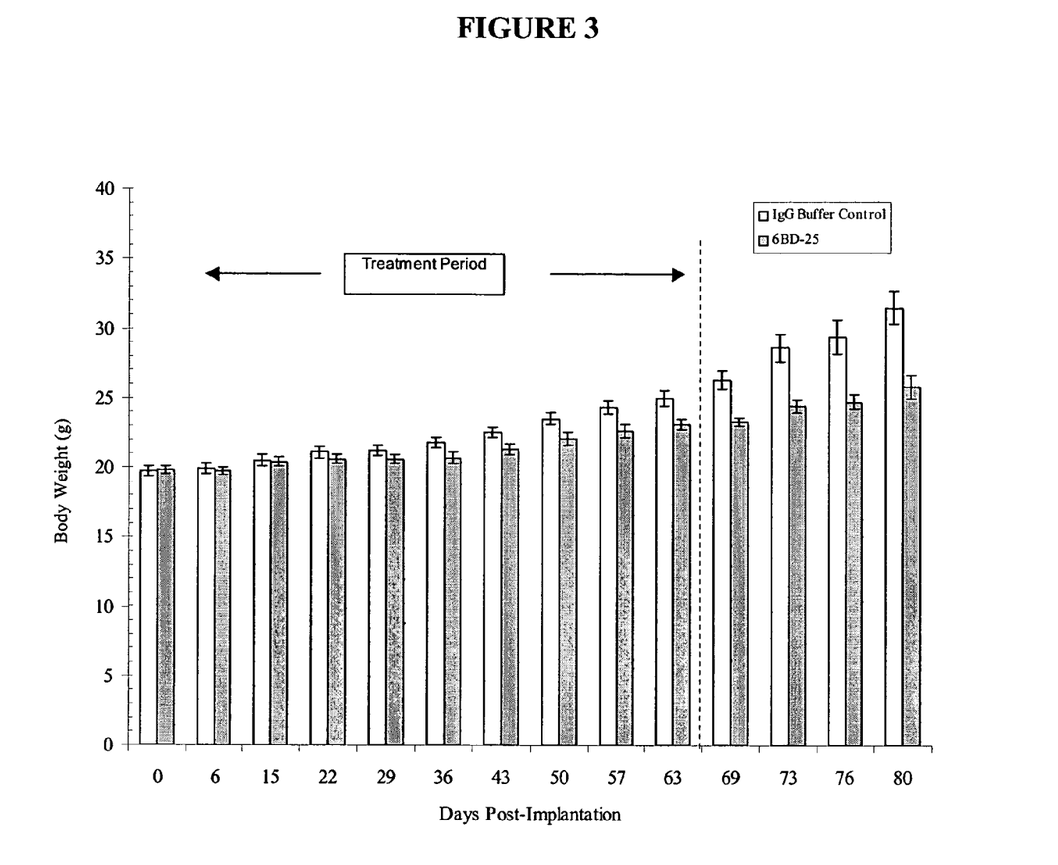
FIG. 3. Effect of 6BD-25 on body weight in a preventative OVCAR-3 ovarian cancer model. The dashed line indicates the period during which the antibody was administered. Data points represent the mean +/−SEM.
Figure 4:
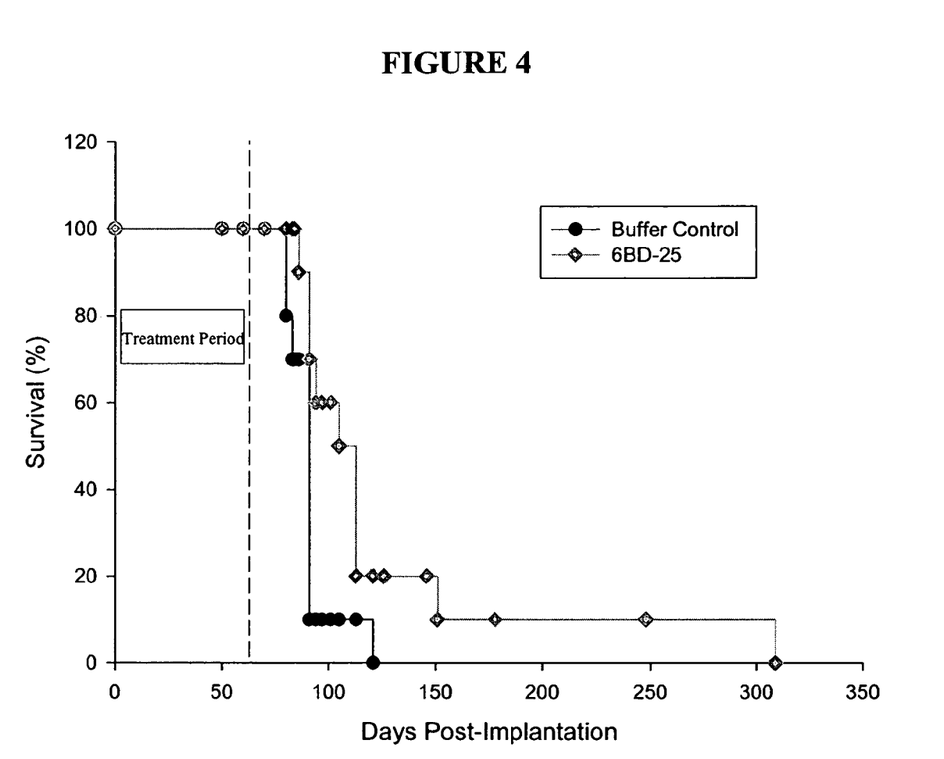
FIG. 4. Survival of tumor-bearing mice after treatment with 6BD-25 or buffer control. Mice were monitored for survival for over 240 days post-treatment.

Body weight was measured roughly every 7th day for up to 11 weeks or until individual animals reached the Canadian Council for Animal Care (CCAC) end-points or day 76. Body weights of the animals were recorded for the duration of the study. At the end of the study all animals were euthanised according to CCAC guidelines.

There were no clinical signs of toxicity throughout the study. Body weight was used as a surrogate measure of tumor progression (FIG. 3). Increased body weight is indicative of tumor burden since the weight gain is caused by ascites formation. Significance was determined using the Dunnett's t-test. At day 80 post-implantation (16 days after the end of treatment), mice in the 6BD-25 treatment group had body weights significantly less than the buffer control group (p=0.002). There was also enhanced survival with treatment with 6BD-25 compared to the buffer control (FIG. 4) as determined by the log-rank test. Mice in the control group had a median survival of 87.0 days versus 107.5 days in the 6BD-25 treatment group (p<0.02). Also, all mice in the buffer treatment group had died by day 120 post-implantation (56 days after treatment). In the antibody treatment group, there was still 1 mouse alive at day 250 post-treatment (186 days post-treatment). In summary, 6BD-25 antibody treatment prevented tumor burden in comparison to buffer control in another well-recognized model of human cancer disease. 6BD-25 also enhanced survival in an ovarian xenograft model.

In toto, 6BD-25 is significantly more effective than buffer control in suppressing tumor growth in a preventative tumor xenograft model of colon and ovarian cancer in SCID mice. Treatment with 6BD-25 also showed a survival benefit in a well-recognized model of human ovarian cancer disease suggesting pharmacologic and pharmaceutical benefits of this antibody for therapy in other mammals, including man. Furthermore, the undetectable or low level of antigen expression on the SW1116 and OVCAR-3 cells respectively, illustrates that the level of antigen expression does not necessarily correlate with in vivo efficacy.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. The isolated monoclonal antibody produced by the hybridoma deposited with the ATCC as Accession Number PTA-5690.

2. A humanized antibody produced from the isolated monoclonal antibody of claim 1.

3. Antigen binding fragments of the isolated monoclonal antibody of claim 1.

4. Antigen binding fragments of the humanized antibody of claim 2.

5. The isolated monoclonal antibody or antigen binding fragments of any one of claims 1, 2, 3, or 4 conjugated with a member selected from the group consisting of toxins, enzymes, radioactive compounds, and hematogenous cells.

6. The isolated hybridoma deposited with the ATCC as Accession Number PTA-5690.

7. A binding assay to determine presence of cancerous cells in a tissue sample selected from a human colon tumor comprising:
   providing a tissue sample from said human colon tumor;
   providing an isolated monoclonal antibody produced by the hybridoma deposited with the ATCC as Accession Number PTA-5690 or antigen binding fragment thereof; or an antibody conjugate thereof;
   contacting said isolated monoclonal antibody or antigen binding fragment thereof or antibody conjugate thereof with said tissue sample; and
   determining binding of said isolated monoclonal antibody or antigen binding fragment thereof or antibody conjugate thereof with said tissue sample;
   whereby the presence of said cancerous cells in said tissue sample is indicated.

8. A process of isolating or screening for cancerous cells in a tissue sample selected from a human colon tumor comprising:
   providing a tissue sample from said human colon tumor;
   providing an isolated monoclonal antibody produced by the hybridoma deposited with the ATCC as Accession Number PTA-5690 or antigen binding fragment thereof; or an antibody conjugate thereof;
   contacting said isolated monoclonal antibody or antigen binding fragment thereof or antibody conjugate thereof with said tissue sample; and
   determining binding of said isolated monoclonal antibody or antigen binding fragment thereof or antibody conjugate thereof with said tissue sample;
   whereby said cancerous cells are isolated by said binding and their presence in said tissue sample is confirmed.

* * * * *

UNITED STATES PATENT AND TRADEMARK OFFICE
CERTIFICATE OF CORRECTION

Page 1 of 1

| | |
|---|---|
| PATENT NO. | : 7,442,776 B2 |
| APPLICATION NO. | : 10/810163 |
| DATED | : October 28, 2008 |
| INVENTOR(S) | : Ryono et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 841 days.

Signed and Sealed this
Twelfth Day of June, 2012

David J. Kappos
*Director of the United States Patent and Trademark Office*